United States Patent [19]
Hutchison

[11] Patent Number: 4,816,474
[45] Date of Patent: Mar. 28, 1989

[54] AMINO SUBSTITUTED THIENOTHIOPYRAN DERIVATIVES, COMPOSITION CONTAINING THEM, AND METHOD OF USING THEM TO STIMULATE PRESYNAPTIC DOPAMINE RECEPTORS

[75] Inventor: Alan J. Hutchison, Verona, N.J.

[73] Assignee: Ciba-Geigy Corporation, Ardsley, N.Y.

[21] Appl. No.: 20,053

[22] Filed: Feb. 27, 1987

[51] Int. Cl.$^4$ .................. A61K 31/38; C07D 495/04
[52] U.S. Cl. .................... 514/432; 540/596; 546/197; 546/256; 546/270; 548/526; 549/23
[58] Field of Search ............... 540/596; 546/196; 548/526; 549/15, 23; 514/218, 321, 422, 434, 432

[56] References Cited

PUBLICATIONS

D. Binder, et al., Arch. Pharm (Weinheim) 318, pp. 70–78 (1985).
P. Cagniant et al., Bull. Soc. Chim. France 1966, pp. 2172–2179.
G. S. Ponticello, et al., J. Med. Chem. 30 pp. 591–597 (1987).
P. Cagniant et al., Eur. J. Med. Chem. -Chim. Thera. 1980 pp. 439–447.
Aldrich Catalog Handbook of Fine Chemicals (1981–82) pp. 226, 609, 616, 660.
Blicke et al., J. Am. Chem. 68 (1946) pp. 1934–1936.
Shirley et al., J. Med. Chem 9 (1966) pp. 607–609.

Primary Examiner—Mary C. Lee
Assistant Examiner—Kurt G. Briscoe
Attorney, Agent, or Firm—Norbert Gruenfeld

[57] ABSTRACT

Disclosed are compounds of the formula

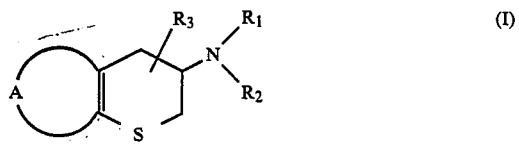

(I)

wherein A represents the divalent radical $—S—CR_4=CR_5—$ in which $R_4$ and $R_5$ independently represent hydrogen or lower alkyl; $R_1$ represents hydrogen, lower alkyl or aryl-lower alkyl; $R_2$ represents hydrogen, lower alkyl or aryl-lower alkyl; or $R_1$ and $R_2$ combined represent alkylene of 4 to 6 carbon atoms; $R_3$ represents hydrogen or lower alkyl; an S-oxide thereof; or a pharmaceutically acceptable salt thereof; which are useful as presynaptic dopamine receptor agonists for the treatment of central nervous system disorders; processes for preparing same; and pharmaceutical compositions comprising said compounds.

19 Claims, No Drawings

AMINO SUBSTITUTED THIENOTHIOPYRAN DERIVATIVES, COMPOSITION CONTAINING THEM, AND METHOD OF USING THEM TO STIMULATE PRESYNAPTIC DOPAMINE RECEPTORS

SUMMARY OF THE INVENTION

The present invention is concerned with 5,6-dihydro-4H-thieno[2,3-b]thiopyran-5-amines and 6,7-dihydro-5H-thieno[3,2-b]thiopyran-6-amines useful as central nervous system receptor modulators, particularly as presynaptic dopamine receptor agonists for the treatment of central nervous system disorders, processes for preparing same, pharmaceutical compositions comprising said compounds, and a method of stimulating presynaptic dopamine receptors in mammals and of treating syndromes, conditions and diseases in mammals responsive to the effect of such a presynaptic dopamine receptor agonist by administration of a said compound or a pharmaceutical composition comprising a said compound.

DETAILED DESCRIPTION OF THE INVENTION

Particularly, the invention is concerned with dihydro-thienothiopyran derivatives of the formula

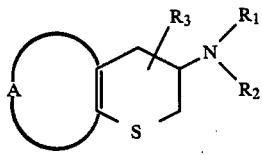 (I)

wherein A represents the divalent radical —S—CR$_4$=CR$_5$— in which R$_4$ and R$_5$ independently represent hydrogen or lower alkyl; R$_1$ represents hydrogen, lower alkyl or aryl-lower alkyl; R$_2$ represents hydrogen, lower alkyl or aryl-lower alkyl; or R$_1$ and R$_2$ combined represent alkylene of 4 to 6 carbon atoms; R$_3$ represents hydrogen or lower alkyl; S-oxides thereof; and pharmaceutically acceptable salts thereof.

A particular embodiment of the invention is concerned with the 5,6-dihydro-4H-thieno[2,3-b]thiopyran derivatives of formula Ia

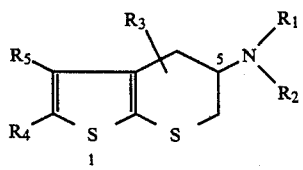 (Ia)

wherein R$_1$ to R$_5$ have meaning as defined above; S-oxides thereof; and pharmaceutically acceptable salts thereof.

Another particular embodiment of the invention is concerned with the 6,7-dihydro-5H-thieno[3,2-b]thiopyran derivatives of formula Ib

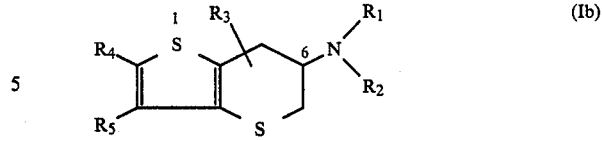 (Ib)

wherein R$_1$ to R$_5$ have meaning as defined above; S-oxides thereof; and pharmaceutically acceptable salts thereof.

Preferred are said compounds of formula I, Ia or Ib wherein R$_1$ and R$_2$ independently represent hydrogen, lower alkyl or aryl-lower alkyl; or R$_1$ and R$_2$ combined represent butylene or pentylene; R$_3$, R$_4$ and R$_5$ represent hydrogen or lower alkyl; and pharmaceutically acceptable salts thereof.

Further preferred are the compounds of formula I, Ia or Ib wherein R$_1$ represents lower alkyl; R$_2$ represents lower alkyl or aryl-lower alkyl; R$_3$, R$_4$ and R$_5$ represent hydrogen; and pharmaceutically acceptable salts thereof.

Particularly preferred are the compounds of formula I, Ia or Ib wherein R$_1$ and R$_2$ represent lower alkyl; R$_3$, R$_4$ and R$_5$ represent hydrogen; and pharmaceutically acceptable salts thereof.

Further preferred are said compounds of formula I, Ia or Ib wherein R$_1$ and R$_2$ are advantageously identical and represent straight chain alkyl of 1 to 4 carbon atoms; R$_3$, R$_4$ and R$_5$ represent hydrogen; and pharmaceutically acceptable salts thereof.

Preferred in turn are the said compounds of formula Ia as disclosed hereinabove.

The general definitions used herein have the following meaning within the scope of the present invention.

The term "lower" referred to above and hereinafter in connection with organic radicals or compounds respectively defines such with up to and including 7, preferably up to and including 4 and advantageously one or two carbon atoms.

A lower alkyl group contains 1 to 7 carbon atoms, preferably 1 to 4 carbon atoms, is advantageously straight chain and represents for example methyl, ethyl, propyl or butyl.

Alkylene of 4 to 6 carbon atoms (for R$_1$ and R$_2$ combined) represents preferably straight chain butylene, pentylene and hexylene to form together with the nitrogen atom pyrrolidino, piperidino and perhydroazepino respectively.

Aryl represents a carbocyclic or heterocyclic aromatic radical.

Aryl is preferably phenyl or phenyl substituted by one to three of lower alkyl, halogen or lower alkoxy; pyridyl; or thienyl.

Aryl-lower alkyl is preferably benzyl or 2-phenylethyl, optionally substituted on the phenyl ring as defined under aryl.

S-Oxides represent mono-S-oxide (sulfoxide) or di-S-oxide (sulfonyl) derivatives, preferably at the sulfur atom in the six membered thiopyran ring.

Depending on the nature of substituents and the resulting number of asymmetric carbon atoms, the compounds of the invention exist in the form of a number of racemates and optical antipodes thereof. Thus compounds of the invention can exist in the form of stereoisomers, e.g. diastereoisomers, racemates, pure enantiomers or mixtures thereof, all of which are within the scope of the invention.

Pharmaceutically acceptable salts are therapeutically acceptable acid addition salts, preferably salts of inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The novel compounds of the invention are active in state of art in vitro and in vivo test systems indicative of presynaptic dopamine receptor agonist activity. Selective presynaptic dopamine receptor agonists can be used e.g. for the treatment of dyskinesias, parkinsonism or psychotic conditions such as schizophrenia.

The above-cited properties are demonstrable in vitro and in vivo tests, using advantageously mammals, e.g. rats, dogs, monkeys or isolated organs, tissues and preparations thereof. Said compounds can be applied in vitro in the form of solutions, e.g. preferably aqueous solutions, and in vivo either enterally or parenterally, advantageously orally or intravenously, e.g. within gelain capsules, as starch suspensions or in aqueous solutions. The dosage in vitro may range between about $10^{-4}$ molar and $10^9$ molar concentrations. The dosage in vivo may range preferably between about 0.01 and 50 mg/kg/day, advantageously between about 0.05 and 20 mg/kg/day.

The presynaptic dopamine receptor binding properties indicative of the presynaptic dopamine receptor regulatory, e.g. agonistic activity, of the compounds of the invention can be determined in the dopamine binding assay in vitro by the following method involving the displacement of the dopamine agonist 2-amino-6,7-dihydroxy-1,2,3,4-tetrahydronaphthalene ($^3$H-ADTN) from membranes of calf-caudate nucleus.

In the binding assay, triplicate 2 ml samples (equivalent to 5 mg/ml of brain tissue) of the calf brain caudate nucleus membrane suspension are incubated for 60 minutes at 25° C. with 0.2 nM $^3$H-ADTN without or in the presence of various concentrations of test compound in solvent. The reaction is terminated by filtering with 5 ml of cold 50 mM Tris-HCl buffer pH 7.7. The filters are placed in scintillation vials with 5 ml of scintillation solution, disrupted by vigorous mechanical shaking for 90 minutes, and counted for radioactivity.

The $IC_{50}$ values which represent the concentration of test compounds required to inhibit the specific binding of 0.2 nM $^3$H-ADTN by 50% are determined graphically.

The in-vivo presynaptic dopamine agonist activity (also called dopamine autoreceptor agonist activity) is determined in the rat gamma-butyrolactone (GBL) model by a modification of the procedure described by Walters and Roth, Naunyn Schmiedeberg's Arch. Pharmacol. 296, 5 (1976). In this model, a presynaptic dopamine agonist inhibits the GBL-induced accumulation of the dopamine precursor DOPA in the brain after pretreatment with 3-hydroxybenzylhydrazine (NDS-1015), a DOPA decarboxylase inhibitor.

Test compounds are dissolved in 0.9% saline, with sodium metabisulfite to prevent oxidation, if required. Animals are treated with i.p. injections of solutions of test compounds or saline, followed by gamma-butyrolactone (GBL, 750 mg/kg i.p.) or saline for control animals 15 minutes later, and finally with NSD-1015 (100 mg/kg i.p.) 5 minutes after the administration of GBL. Thirty minutes after the administration of NSD-1015, animals are sacrificed, brains are removed, and striatae are isolated, then frozen at −70° C. until deproteinization, extraction and analysis. The ED50 (dose at which the DOPA accumulation is inhibited by 50%) values are determined by plotting the percent inhibition of DOPA accumulation versus $log_{10}$ of the dose of test compound administered. The same method is also applicable to oral administration of the test compounds.

The selectivity of the compounds of the invention as to pre-synaptic dopamine agonist activity is determined in vitro by binding studies in displacing $^3$H-spiroperidol from post-synaptic dopamine receptors. Weak binding in this latter assay is indicative of selectivity.

In vivo such selectivity can be determined by measurement of the degree of reversal of reserpine induced hypomotility in the rat, described in Life Sciences 28, 1225 (1981). The relative absence of such reversal at effective doses (e.g. in the GBL model) is indicative of selective presynaptic dopamine agonist activity.

Illustrative of the invention, 5-dipropylamino-5,6-dihydro-4H-thieno[2,3-b]thiopyran hydrochloride has an $IC_{50}$ of about $1.5 \times 10^{-7}$M in the $^3$H-ADTN presynaptic dopamine receptor assay.

Also illustrative of the invention, 5-dipropylamino-5,6-dihydro-4H-thieno[2,3-b]thiopyran displays an ED50 of about 2.6 mg/kg i.p. and 5.6 mg/kg p.o. in the GBL model in the rat.

The aforesaid advantageous properties render the compounds of the invention useful as therapeutic agents with neurotropic properties. They exhibit selective central nervous system presynaptic dopamine receptor stimulating activity and as such are useful in mammals, particularly as neuroleptic (antipyschotic) agents.

The compounds of the invention can be prepared using the following processes:

(a) condensation of a compound of the formula II

or an S-mono- or di-oxide thereof wherein A and $R_3$ have meaning as previously defined above, X represents oxo, or X represents reactive esterified hydroxy together with hydrogen, with a compound of the formula III

wherein $R_1$ and $R_2$ have meaning as previously defined; or (b) alkylation of a compound of the formula IV

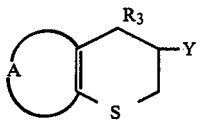

or an S-mono- or di-oxide thereof wherein A and R₃ have meaning as defined above, and Y represents NH₂, NHR₁ or NHR₂, with a reactive ester derivative of a lower alkanol $$R_1-OH \text{ or } R_2-OH \qquad (V),$$

wherein R₁ and R₂ have meaning as previously defined, or with an aldehyde corresponding to R₁—OH or R₂—OH, under reductive conditions; or (c) reduction of a compound of the formula VI

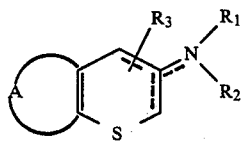

or an S-mono- or di-oxide thereof wherein A and R₁-R₃ have meaning as defined above, and the bonds with dotted lines represent a double bond situated at any of the indicated positions;

(d) reduction of a compound of formula VII

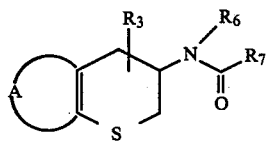

or an S-mono- or di-oxide thereof wherein R₆ represents R₁ or R₂; A, R₁-R₃ have meaning as defined above; and R₇ represents lower alkyl with 1 to 6 carbon atoms, aryl-lower alkyl with 1 to 6 carbon atoms, or hydrogen;

(e) rearrangement of a derivative, e.g. an azide, primary amide, N-hydroxyamide or N-acyloxyamide derivative, of a carboxylic acid of the formula VIII

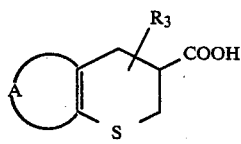

wherein A and R₃ have meaning as defined above, or an S-mono or di-oxide thereof, to yield a compound of formula I wherein R₁ and R₂ represent hydrogen; and, if desired, converting a resulting compound of the invention into another compound of the invention, and/or, if desired, converting a resulting free compound into a salt or a resulting salt into a free compound or into another salt, and/or, if required, separating a mixture of isomers or racemates obtained into the single isomers or racemates, and/or, if desired, resolving a racemate obtained into the optical antipodes.

A reactive esterified hydroxy group (reactive ester of an alcohol) in any of the above mentioned processes is hydroxy esterified by a strong acid, especially a strong inorganic acid, such as a hydrohalic acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example methylsulfonyloxy or 4-methylphenylsulfonyloxy (tosyloxy).

In starting compounds and intermediates which are converted to the compounds of the invention in a manner described herein, functional groups present are optionally protected by conventional protecting groups that are common in preparative organic chemistry.

Well-known protecting groups and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1981, and also in Houben-Weyl, "Methoden der Organischen Chemie", Vol. 15/1, George Thieme Verlag, Stuttgart, 1974.

The preparation of the compounds of the invention according to process (a) is carried out according to procedures known in the art for N-alkylation reactions.

The preparation of compounds of the invention by reductive N-alkylation when X represents oxo is carried out under conditions known to the art, e.g. with chemical reducing agents such as hydride reducing agents, e.g. an alkali metal cyanoborohydride such as sodium cyanoborohydride. The reductive amination with an alkali metal cyanoborohydride is preferably carried out in an inert solvent, e.g. methanol or acetonitrile, advantageously in the presence of an acid, e.g. hydrochloric acid or acetic acid.

The preparation of the compounds of the invention by process (a) when X represents reactive esterified hydroxy together with hydrogen is carried out with or without basic catalysts such as triethylamine or potassium carbonate in an inert solvent, under conditions well-known in the art for N-alkylation reactions.

The preparation of the compounds of the invention according to process (b) is carried out under conditions described above for process (a), e.g. for N-alkylation when the starting material is a reactive ester of R₁—OH or R₂—OH, and under conditions described under process (a) for reductive N-alkylation when the starting material is an aldehyde (a lower alkylcarboxaldehyde or an aryl-lower alkylcarboxaldehyde).

The preparation of the compounds of the invention according to process (c) is carried out according to procedures known in the art for the saturation of carbon to nitrogen or enamine carbon to carbon double bonds, e.g. with a chemical reducing agent such as sodium cyanoborohydride under conditions known in the art e.g. at room or elevated temperature in a polar solvent such as isopropanol.

The preparation of the compounds of the invention according to process (d) is carried out according to procedures known in the art for the reduction of an amide group, e.g. by reduction with a hydride reducing agent e.g. lithium aluminum hydride or borane (diborane) in an inert solvent such as tetrahyrofuran or diethyl ether, advantageously at room or elevated temperature.

The rearrangement according to process (e) of carboxylic acid derivatives is carried out according to procedures well known in the art, e.g. the Hofmann rearrangement of amides, the Curtius rearrangement of acyl azides, the Lossen rearrangement of N-acyloxyamides, and the Schmidt rearrangement by treatment of the carboxylic acid with hydrazoic acid.

The ketone starting materials of formula II, the optionally substituted 5,6-dihydro-4H-thieno[2,3-b]thiopyran-5-ones and 6,7-dihydro-5H-thieno[3,2-b]-thiopyran-6-ones, can be prepared e.g. by first condensing e.g. an optionally substituted thiophene-2- or 3-thiol with alpha-(halomethyl)-acrylic acid followed by cyclization of the resulting alpha-(thiophenethiomethyl)-acrylic acid at elevated temperature to obtain the optionally substituted 5,6-dihydro-4H-thieno-[2,3-b]thiopyran-5-carboxylic acid or 6,7-dihydro-5H-thieno-[3,2-b]thiopyran-6-carboxylic acid (of general formula VIII below). Dehydrogenation, e.g. by treatment with N-chlorosuccinimide, yields the corresponding 4H-thieno[2,3-b]thiopyran-5-carboxylic acid or 5H-thieno[3,2-b]thiopyran-6-carboxylic acid. Subsequent degradation to the amine, e.g. via the azide, and subsequent acid hydrolysis yields the corresponding 5,6-dihydro-4H-thieno[2,3-b]thiopyran-5-one or 6,7-dihydro-5H-thieno[3,2-b]thiopyran-6-one, respectively.

Alternately, an optionally substituted 4H-thieno[2,3-b]thiopyran or 5H-thieno[3,2-b]thiopyran is reacted with a halogenating agent, e.g. N-bromosuccinimide or N-bromoacetamide in a hydroxylating solvent such as aqeuous acetone, followed by a nonaqueous base, e.g. sodium hydride in tetrahydrofuran, to yield the correspondingly substituted epoxide. Rearrangement with an acidic reagent, advantageously zinc iodide in toluene, results in the corresponding ketones of formula II.

The primary and secondary 5-amino-5,6-dihydro-4H-thieno[2,3-b]thiopyrans and 6-amino-6,7-dihydro-5H-thieno[3,2-b]thiopyans of formula IV for process (b) can be prepared from the intermediates of formula II by reaction with ammonia, a primary amine ($R_1 NH_2$ or $R_2 NH_2$), or preferably an acid addition salt thereof, in the presence of a reducing agent, advantageously sodium cyanoborohydride, when X represents oxo.

The primary amines of formula IV for process (b) are prepared e.g. by Curtius degradation of the corresponding 5,6-dihydro-4H-thieno[2,3-b]thiopyran-5-carboxylic acid or 6,7-dihydro-5H-thieno[3,2-b]thiopyran-6-carboxylic acid (the preparation of which are described above), e.g. with diphenylphosphoryl azide or as described under process (e) and in the examples.

The intermediates of formula VI may be prepared by treatment of the correspondingly substituted ketones, of formula II wherein X represent oxo, with an amine of the formula III under dehydrating conditions, e.g. in the presence of molecular sieves, boron trifluoride etherate or p-toluenesulfonic acid in an inert solvent such as toluene or methylene chloride.

The intermediates of formula VII may be prepared by acylation of a compound of formula IV wherein Y represents $NHR_1$ or $NHR_2$ with a carboxylic acid of the formula $R_7$-COOH wherein $R_1$, $R_2$ and $R_7$ have meaning as defined above, in the presence of a condensing agent such as dicyclohexylcarbodiimide, or with a reactive functional derivative thereof, e.g. an acyl halide such as the acid chloride, or a mixed anhydride, e.g. such derived from a lower alkyl halocarbonate such as ethyl chloroformate, in an inert solvent such as methylene chloride, preferably in the presence of a basic catalyst such as pyridine.

The carboxylic acids of formula VIII (also intermediates for the preparation of compounds of formula (II) which are prepared as described above and as illustrated in the examples, are converted to the corresponding primary amide, azide or N-acyloxyamide derivatives by methods well-known in the art, e.g. to the azide with diphenylphosphoryl azide, to the N-acyloxyamide by first converting the carboxylic acid to a lower alkyl ester, then to the hydroxamic acid which is then acylated with e.g. an acid chloride.

The compounds of the invention obtained by any of the methods described above and intermediates can be converted into each other according to conventional methods known to the art.

For example, primary amines may be converted to secondary amines and secondary amines may be converted to tertiary amines by standard methods known in the art.

Similarly, the compounds of formula I or intermediates may be converted to the corresponding sulfoxides and sulfones by treatment with e.g. a peracid, preferably m-chloroperbonzoic acid, to obtain either the mono-S-oxide (sulfoxide) or di-S-Oxide (sulfone) depending on the quantity of peracid used. The sulfoxides may also be prepared by treatment with a salt of periodic acid, e.g. sodium periodate.

Furthermore, a compound of formula Ia or Ib wherein $R_4$ represents hydrogen, and in which $R_1$ and $R_2$ do not represent hydrogen, can be converted to a corresponding compound wherein $R_4$ represents lower alkyl by reaction first with a strong base, such as butyl lithium, in an anhydrous inert solvent, such as tetrahydrofuran, and subsequent treatment with e.g. a lower alkyl halide.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point for the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Whenever desirable, the above processes are carried out after first suitably protecting any potentially interfering reactive functional groups, as illustrated above and in the examples herein.

Advantageously, those starting materials should be used in said reactions, that lead to the formation of those compounds indicated above as being preferred.

The invention also relates to novel starting materials and processes for their manufacture.

Depending on the choice of starting materials and methods, the new compounds may be in the form of one of the possible isomers or mixtures thereof, for example, as pure geometric isomers (cis or trans), as pure optical isomers (as antipodes), or as mixtures of optical isomers such as racemates, or as mixtures of geometric isomers.

In case geometric or diastereomeric mixtures of the above compounds or intermediates are obtained, these can be separated into the single racemic or optically active isomers by methods in themselves known, e.g. by fractional distillation, crystallization and/or chromatography.

The racemic products of the invention or basic intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Advantageously, the more active of the antipodes of the compounds of this invention is isolated.

Finally, the compounds of the invention are either obtained in the free form, or as a salt thereof. Any resulting base can be converted into a corresponding acid addition salt, preferably with the use of a pharmaceutically acceptable acid, or resulting salts can be converted into the corresponding free bases, for example, with the use of a stronger base, such as a metal or ammonium hydroxide, or any basic salt, e.g., an alkali metal hydroxide or carbonate. These or other salts, for example, the picrates, can also be used for purification of the bases obtained. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention also relates to pharmaceutical compositions, especially pharmaceutical compositions having presynaptic dopamine receptor stimulating activity, comprising an effective amount of a compound of the invention in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral, transdermal or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salts and/or polyethylene glycol; for tablets also (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The inention also relates to a method of stimulating presynaptic dopamine receptors in mammals which comprises administering to a mammal an effective amount of a compound of the invention, preferably in the form of the above-cited pharmaceutical compositions. The invention further relates to a method of treatment in mammals of central nervous system disorders responsive to presynaptic dopamine receptor stimulation, such as dyskinesias, parkinsonism and in particular psychotic disorders such as schizophrenia, using an effective amount of a compound of the invention, as pharmacologically active substance, preferably in the form of the above-cited pharmaceutical compositions. The dosage of active compound administered is dependent on the species of warm-blooded animal (mammal), the body weight, age and individual condition, and on the form of administration.

A unit dosage for a mammal of about 50 to 70 kg may contain between about 10 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Unless mentioned otherwise, alkyl, e.g. propyl, refers to straight chain alkyl, e.g. n-propyl.

EXAMPLE 1

(a) A mixture of 10.0 g of 5,6-dihydro-4H-thieno[2,3-b]thiopyran-5-(N-benzoyloxy)-carboxamide and 195 ml of 0.165 molar sodium ethoxide solution in ethanol is heated under reflux for 3 hours, and filtered. The filtrate is evaporated to dryness and the residue extracted with 60 ml of ether. The ether extract is washed with 50 ml of 10% sodium hydroxide solution, and then with saturated ammonium chloride solution, dried over magnesium sulfate and evaporated to dryness to yield 5-ethoxycarbonylamino-5,6-dihydro-4H-thieno[2,3-b]thiopyran as an oil.

A mixture of 5.3 g of 5-ethoxycarbonylamino-5,6-dihydro-4H-thieno[2,3-b]thiopyran, 20 ml of 26% aqueous sodium hydroxide and 20 ml of 1,2-propanediol is heated at 140° for 3 hours. The reaction mixture is cooled and carefully acidified with 29 ml of 6N hydrochloric acid leading to evolution of gas. The resulting mixture is basified with 50% sodium hydroxide solution and extracted with ethyl acetate. The ethyl acetate extract is evaporated to dryness, the residue is dissolved in ether, the ether solution is washed with water and evaporated to dryness. The residue is dissolved in 40 ml of ethyl acetate and 41 ml of a solution of hydrogen chloride in ethyl acetate (0.535 molar) is added. The resulting precipitate is collected and dried to yield 5,6-dihydro-4H-thieno[2,3-b]thiopyran-5-amine hydrochloride.

The starting material is prepared as follows:
A solution of thiophene (16.8 g) in 50 ml of tetrahydrofuran is cooled to −10° and a solution of 0.2 mole of n-butyllithium in hexane is added while cooling at −10° at a rate so as to maintain temperature at about −5°, under nitrogen atmosphere. The reaction mixture is stirred −10° to −5° for 30 minutes, 6.4 g of granular sulfur is added slowly and the reaction mixture is then stirred at −5° to 0° for two hours. A cold solution of 33.0 g of alpha-(bromomethyl)-acrylic acid dissolved at 0° in a solution of 8.3 g of sodium hydroxide in 125 ml of water is then added slowly while cooling so as to maintain the temperature below 10°. After stirring for one hour at 0° to 5°, the reaction mixture is warmed slowly, over two hours to about 20°, extracted twice with toluene (25 ml), and the toluene extracts are washed once with a saturated sodium chloride solution (25 ml).

The aqueous phase and aqueous wash are combined, treated with charcoal and filtered through hyflo. The basic aqueous solution is then diluted with water (150–250 ml), treated with 6N HCl (40 ml) to obtain a final pH of 1.0–2.0, and stirred for 30 minutes at 20°. The precipitated product is collected, washed with water and dried to yield alpha-[(2-thienyl)-thiomethyl]-acrylic acid; Rf=0.75 using silica gel and toluene/ethyl acetate/acetic acid [70:30:10] as eluent.

A solution of 95.0 g of alpha-[(2-thienyl)-thiomethyl]-acrylic acid in 190 ml of dimethylformamide is heated at 135° for 40 minutes and then evaporated under reduced pressure at 100° to a volume of about 135 ml. The residue is diluted with 400 ml of t-butyl methyl ether, 81.3 g of dicyclohexylamine is added, and the reaction mixture is stirred at room temperature overnight. The crystallized product is collected, washed with t-butyl methyl ether and dried to yield dicyclohexylammonium 5,6-dihydro-4H-thieno[2,3-b]thiopyran-5-carboxylate; Rf=0.63 using silica gel and toluene/ethyl acetate/acetic acid (70:30:10) as eluent.

Concentrated sulfuric acid (6.84 g) is added to a mixture of 25.0 g of dicyclohexylammonium 5,6-dihydro-4H-thieno[2,3-b]thiopyran-5-carboxylate, 100 ml of methanol and 100 ml of toluene. The reaction mixture is heated under reflux for 4½ hours and concentrated in vacuo. Ethyl acetate (50 ml) and water (50 ml) are added. The ethyl acetate layer is separated and the aqueous is extracted with ethyl acetate (45 ml). The combined ethyl acetate extracts are washed first with dilute sulfuric acid, then with dilute ammonium hydroxide, and then with sodium chloride solution, with water, dried and evaporated to dryness so yield methyl 5,6-dihydro-4H-thieno[2,3-b]thiopyran-5-carboxylate which is purified by distillation.

A solution of 8.7 g of potassium hydroxide pellets in 25 ml of absolute methanol is added to a solution of 5.9 g of hydroxylamine hydrochloride in 35 ml of absolute methanol. To the mixture under nitrogen atmosphere is added 9.1 g of methyl 5,6-dihydro-4H-thieno[2,3-b]thio-pyran-5-carboxylate. After 1 hour, the mixture is evaporated to dryness. Water (36 ml) and ethyl acetate (36 ml) are added, the mixture is stirred at room temperature, and acidified with 5.5 ml of concentrated hydrochloric acid over 10 to 15 minutes. The ethyl acetate layer is separated, the aqeuous layer is further extracted with ethyl acetate and the combined ethyl acetate extracts are evaporated to dryness. The residue is crystallized from methylene chloride to yield 5,6-dihydro-4H-thieno[2,3-b-thiopyran- 5-(N-hydroxy)-carboxamide.

A solution of 9.79 g of benzoyl chloride in 45 ml of methylene chloride is added to dropwise to a solution of 15.0 g of 5,6-dihydro-4H-thieno[2,3-b]thiopyran-5-(N-hydroxy)-carboxamide and 7.05 g of triethylamine in 105 ml of methylene chloride maintaining a temperature of 0° to 5°. The reaction mixture is allowed to warm to 10°, and 150 ml of water is added in 4 portions. The precipitated product is collected and dried to yield 5,6-dihydro-4H-thieno[2,3-b]thiopyran-5-(N-benzoyloxy)-carboxamide.

(b) Starting with 3-thiophenethiol, 6,7-dihydro-5H-thieno[3,2-b]thiopyran-6-amine is obtained.

EXAMPLE 2

(a) Sodium hydroxide solution (50%, 700 ml) is added in portions to a mixture of 114.65 g of 5,6-dihydro-4H-thieno[2,3-b]thiopyran-5-amine hydrochloride, 940 g of n-propyl iodide and 18.3 g of tetra-n-butylammonium bromide in 700 ml of toluene. The reaction mixture is heated under reflux at 100° for 20 hours. The organic layer is separated and the aqueous phase is extracted with 300 ml of toluene. The combined toluene extracts are washed with water dried and concentrated under vacuo (so as to remove any remaining n-propyl iodide). The residue is then distilled under high vacuum to obtain N,N-dipropyl-5,6-dihydro-4H-thieno[2,3-b]thiopyran-5-amine, b.p. 155°/0.5 mm Hg.

A solution of 4.0 g of N,N-dipropyl-5,6-dihydro-4H-thieno[2,3-b]thiopyran-5-amine in 20 ml of t-butyl methyl ether is slowly added while stirring to a mixture of 5.42 g of 2.4 M ethanolic hydrogen chloride in 45 ml of t-butyl methyl ether. The crystalline product is collected, washed with the solvent and dried to give N,N-dipropyl-5,6-dihydro-4H-thieno[2,3-b]thiopyran-5-amine hydrochloride, m.p. 163°–167°.

Similarly prepared are:
(b) N,N-dibutyl-5,6-dihydro-4H-thieno[2,3-b]thiopyran-5-amine hydrochloride, m.p. 161°–164°;
(c) N,N-diethyl-5,6-dihydro-4H-thieno[2,3-b]thiopyran-5-amine;
(d) N,N-dipropyl-6,7-dihydro-5H-thieno[3,2-b]thiopyran-6-amine.

EXAMPLE 3

A mixture of 9.15 g of 5,6-dihydro-4H-thieno[2,3-b]-thiopyran-5-carboxylic acid, 10 ml of diphenylphosphoryl azide and 6.5 ml of triethylamine in 200 ml of t-butanol is refluxed for 5 hours. After removal of the solvent in vacuo the residue is dissolved in ether and washed with 1N sodium hydroxide. After drying over magnesium sulfate the solvent is removed in vacuo to yield a mixture of N-t-butoxycarbonyl-5,6-dihydro-4H-thieno[2,3-b]-thiopyran-5-amine and N-t-butoxycarbonyl-2-t-butyl-5,6-dihydro-4H-thieno-[2,3-b]thiopyran-5-amine. The mixture is treated with 25 ml of trifluoroacetic acid and refluxed for 15 minutes. After removal of solvent the residue is treated with 40 ml of N-propyl iodide in 100 ml of toluene in the presence of 27 g of sodium carbonate in 150 ml of water. The resulting mixture is refluxed with stirring for 3 days. The solvent is removed from the organic layer and the residue is chromatographed on silica gel to afford 2-t-butyl-N,N-dipropyl-5,6-dihydro-4H-thieno[2,3-b]thiopyran-5-amine (hydrochloride salt, m.p. 227°–233°), and N,N-dipropyl-5,6-dihydro-4H-thieno[2,3-b]thiopyran-5-amine (hydrochloride salt, m.p. 163°–167°) of Example 2.

EXAMPLE 4

A mixture of 8.31 g of 5,6-dihydro-4H-thieno[2,3-b]-thiopyran-5-amine hydrochloride, 17.4 ml of ethyldiisopropylamine, 4.07 g of propionyl chloride in 80 ml of methylene chloride is kept for 30 minutes at room temperature. The reaction mixture is washed with 1N hydrochloric acid and then with saturated sodium bicarbonate solution, the organic layer is dried over magnesium sulfate and the solvent is removed in vacuo to yield N-propionyl-5,6-dihydro-4H-thieno[2,3-b]-thiopyran-5-amine. This is refluxed for 3 hours with 85 ml of 1M borane in tetrahydrofuran. Water and 3N hydrochloric acid are added and the mixture is heated briefly. Basification of the aqueous layer followed by extraction with ether affords an oil after removal of solvent. Addition of ethanolic hydrochloric acid affords N-propyl-5,6-dihydro-4H-thieno[2,3-b]thiopyran-5-amine hydrochloride, m.p. 107°–110°.

EXAMPLE 5

(a) A mixture of 2,5 g of N-propyl-5,6-dihydro-4H-thieno[2,3-b]thiopyran-5-amine hydrochloride, 7.5 g of sodium carbonate, 11 ml of n-butyl iodide 25 ml of toluene and 25 ml of water is refluxed for 3 days. Removal of solvent from the organic layer affords an oil which is treated with ethanolic hydrochloric acid to afford N-butyl- N-propyl-5,6-dihydro-4H-thieno[2,3-b]thiopyran-5-amine hydrochloride, m.p. 161°–164°.

Similarly prepared are:

(b) N-isopropyl-N-propyl-5,6-dihydro-4H-thieno[2,3-b]thiopyran-5-amine hydrobromide;

(c) N-isobutyl-N-propyl-5,6-dihydro-4H-thieno[2,3-b]thiopyran hydrobromide;

(d) N-(2-phenethyl)-N-propyl-5,6-dihydro-4H-thieno[2,3-b]thiopyran-5-amine hydrobromide.

EXAMPLE 6

A mixture of 2.5 g of N,N-dipropyl-5,6-dihydro-4H-thieno[2,3-b]-thiopyran-5-amine in 40 ml of tetrahydrofuran is treated with 4 ml of 2.5 M n-butyl lithium in hexane at 0°. After 30 minutes at 0°, 1.5 g of methyl iodide is added and the mixture is kept at room temperature for 1 hour. Dilution with ether and washing with water followed by drying and removal of the solvent in vacuo affords 2-methyl-N,N-dipropyl-5,6-dihydro-4H-thieno[2,3-b]-thiopyran-5-amine.

EXAMPLE 7

Preparation of 1,000 capsules each containing 10 mg of the active ingredient:

| Formula: | |
|---|---|
| N,N—dipropyl-5,6-dihydro-4H—thieno[2,3-b]thiopyran-5-amine hydrochloride | 10.0 g |
| Lactose | 207.0 g |
| Modified starch | 80.0 g |
| Magnesium stearate | 3.0 g |

Procedure

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

What is claimed is:

1. A compound of the formula

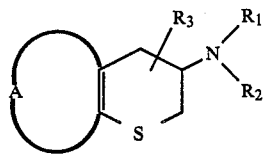

wherein A represents the divalent radical $-S-CR_4=CR_5-$ in which $R_4$ and $R_5$ independently represent hydrogen or lower alkyl; $R_1$ represents hydrogen, lower alkyl or aryl-lower alkyl; $R_2$ represents hydrogen, lower alyl or aryl-lower alkyl; or $R_1$ and $R_2$ combined represent alkylene of 4 to 6 carbon atoms; $R_3$ represents hydrogen or lower alkyl; and aryl in aryl-lower alkyl represents phenyl or phenyl substituted by one to three of lower alkyl, halogen or lower alkoxy; or said aryl represents pyridyl or thienyl; an S-oxide thereof; or a pharmaceutically acceptable salt thereof.

2. A compound according to claim 1 of the formula

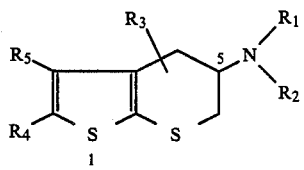

wherein $R_1$ represents hydrogen, lower alkyl or aryl-lower alkyl; $R_2$ represents hydrogen, lower alkyl or aryl-lower alkyl; or $R_1$ and $R_2$ combined represents alkylene of 4 to 6 carbon atoms; $R_3$ represents hydrogen or lower alkyl; $R_4$ and $R_5$ independently represent hydrogen or lower alkyl; and aryl has meaning as defined in claim 1; an S-oxide thereof; or a pharmaceutically acceptable salt thereof.

3. A compound according to claim 1 of the formula

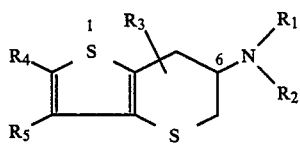

wherein $R_1$ represents hydrogen, lower alkyl or aryl-lower alkyl; $R_2$ represents hydrogen, lower alkyl or aryl-lower alkyl; or $R_1$ and $R_2$ combined represent alkylene of 4 to 6 carbon atoms; $R_3$ represents hydrogen or lower alkyl; $R_4$ and $R_5$ independently represent hydrogen or lower alkyl; and aryl has meaning as defined in claim 1; an S-oxide thereof; or a pharmaceutically acceptable salt thereof.

4. A compound according to claim 1 wherein $R_1$ and $R_2$ independently represent hydrogen, lower alkyl or aryl-lower alkyl; in which aryl represents phenyl or phenyl substituted by one to three of lower alkyl, halogen or lower alkoxy or $R_1$ and $R_2$ combined represent butylene or pentylene; $R_3$, $R_4$ and $R_5$ represent hydrogen or lower alkyl; or a pharmaceutically acceptable salt thereof.

5. A compound according to claim 1 wherein $R_1$ represents lower alkyl; $R_2$ represents lower alkyl or aryl-lower alkyl; in which aryl represents phenyl or phenyl substituted by one to those of lower alkyl, halogen or lower alkoxy $R_3$, $R_4$ $R_5$ represent hydrogen; or a pharmaceutically acceptable salt thereof.

6. A compound according to claim 1 wherein $R_1$ and $R_2$ represent lower alkyl; $R_3$, $R_4$ and $R_5$ represent hydrogen; or a pharmaceutically acceptable salt thereof.

7. A compound according to claim 1 wherein $R_1$ and $R_2$ represent straight chain alkyl of 1 to 4 carbon atoms; $R_3$, $R_4$ and $R_5$ represent hydrogen; or a pharmaceutically acceptable salt thereof.

8. compound according to claim 2 wherein $R_1$ and $R_2$ independently represent hydrogen, lower alkyl or aryl-lower alkyl; in which aryl represents phenyl or phenyl substituted by one to three of lower alkyl, halogen or lower alkoxy $R_3$, $R_4$ and $R_5$ represent hydrogen or lower alkyl; or a pharmaceutically acceptable salt thereof.

9. A compound according to claim 2 wherein $R_1$ represents lower alkyl; $R_2$ represents lower alkyl or aryl-lower alkyl; in which aryl represents phenyl or phenyl substituted by one to three of lower alkyl, halogen or lower alkoxy $R_3$, $R_4$ and $R_5$ represent hydrogen; or a pharmaceutically acceptable salt thereof.

10. A compound according to claim 2 wherein $R_1$ and $R_2$ represent lower alkyl; $R_3$, $R_4$ and $R_5$ represent hydrogen; or a pharmaceutically acceptable salt thereof.

11. A compound according to claim 2 wherein $R_1$ and $R_2$ represent straight chain alkyl of 1 to 4 carbon atoms; $R_3$, $R_4$ and $R_5$ represent hydrogen; and pharmaceutically acceptable salts thereof.

12. A compound according to claim 11 being N,N-dipropyl-5,6-dihydro-4H-thieno[2,3-b]thiopyran-5-amine or a pharmaceutically acceptable salt thereof.

13. A compound according to claim 11 being N,N-dibutyl-5,6-dihydro-4H-thieno[2,3-b]thiopyran-5-amine or a pharmaceutically acceptable salt thereof.

14. A presynaptic dopamine receptor stimulating pharmaceutical composition suitable for administration to a mammal comprising an effective presynaptic dopamine receptor stimulating amount of a compound of claim 1 in combination with one or more pharmaceutically acceptable carriers.

15. A method of stimulating presynaptic dopamine receptors in mammals, comprising the administration to a mammal in need thereof of an effective amount of a compound of claim 1 or of a pharmaceutical composition comprising said compound in combination with one or more pharmaceutically acceptable carriers.

16. A method of treating central nervous system disorders responsive to the stimulation of presynaptic dopamine central nervous system receptors in mammals comprising the administration to a mammal in need thereof of an effective presynaptic dopamine receptor stimulating amount of a compound of claim 1 or of a presynaptic dopamine receptor stimulating pharmaceutical composition comprising a said compound in combination with one or more pharmaceutically acceptable carriers.

17. A method according to claim 16 of treating dyskinesias, parkinsonism or psychotic conditions.

18. A method of treating psychotic disorders in mammals comprising the administration to a mammal in need thereof of an effective antipsychotic amount of a compound of claim 8.

19. A method according to claim 18 comprising the administration of an effective amount of N,N-dipropyl-5,6-dihydro-4H-thieno[2,3-b]thiopyran-5-amine or a pharmaceutically acceptable salt thereof.

* * * * *

UNITED STATES PATENT AND TRADEMARK OFFICE
CERTIFICATE OF CORRECTION

PATENT NO.  : 4,816,474
DATED       : Mar. 28, 1989
INVENTOR(S) : Hutchison

It is certified that error appears in the above-identified patent and that said Letters Patent is hereby corrected as shown below:

In the Claims:

Claim 1, Col. 14, line 13: delete "alyl" and insert ---alkyl---.

Claim 1, Col. 14, lines 13-14: delete "or $R_1$ and $R_2$ combined represent alkylene of 4 to 6 carbon atoms;"

Claim 1, Col. 14, line 17: delete "to three"

Claim 1, Col. 14, line 18: delete "pyridyl or"

Claim 2, Col. 14, lines 32-33: delete "or $R_1$ and $R_2$ combined represent alkylene of 4 to 6 carbon atoms;"

Claim 3, Col. 14, lines 49-50: delete "or $R_1$ and $R_2$ combined represent alkylene of 4 to 6 carbon atoms;"

Correct entire claim 4 to read:

---A compound according to claim 1 wherein $R_1$ and $R_2$ independently represent hydrogen, lower alkyl or aryl-lower alkyl in which aryl represents phenyl or phenylsubstituted by one of lower alkyl, halogen or lower alkoxy; $R_3$, $R_4$ and $R_5$ represent hydrogen; or a pharmaceutically acceptable salt thereof---.

Claim 5, Col. 14, line 66: delete "to those"

Claim 8, Col. 15, line 11: delete "to three"

Claim 9, Col. 15, line 18: delete "to three"

UNITED STATES PATENT AND TRADEMARK OFFICE
CERTIFICATE OF CORRECTION

PATENT NO. : 4,816,474

DATED : Mar. 28, 1989

INVENTOR(S) : Hutchison

It is certified that error appears in the above-identified patent and that said Letters Patent is hereby corrected as shown below:

Claim 17, Col. 16, line 24: delete "psychotic conditions" and insert ---schizophrenia---.

Claim 18, Col. 16, line 25: delete "psychotic disorders" and insert ---schizophrenia---.

Signed and Sealed this

Twenty-second Day of May, 1990

Attest:

HARRY F. MANBECK, JR.

*Attesting Officer*   *Commissioner of Patents and Trademarks*